US00PP30085P2

(12) United States Plant Patent
Hansen

(10) Patent No.: US PP30,085 P2
(45) Date of Patent: Jan. 8, 2019

(54) ***SALVIA* PLANT NAMED 'BUMBLESKY'**

(50) Latin Name: ***Salvia nemorosa* (Linnaeus)**
Varietal Denomination: Bumblesky

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/731,915

(22) Filed: Aug. 22, 2017

(51) Int. Cl.
*A01H 5/02* (2018.01)

(52) U.S. Cl.
USPC ..... Plt./475
CPC ..... *A01H 5/02* (2013.01)

(58) Field of Classification Search
USPC ..... Plt./475
See application file for complete search history.

*Primary Examiner* — Anne Marie Grunberg

(57) ABSTRACT

The new and distinct cultivar of perennial *Salvia* plant named 'Bumblesky' characterized by its small light blue-colored flowers densely arranged in verticils, with compact rounded habit and stiff, upright, branched stems and strong vigorous growth rate and gray-green foliage. *Salvia* 'Bumblesky' is especially useful for landscaping and containerized ornamentals by itself or in combination with other plants.

1 Drawing Sheet

Botanical denomination: *Salvia nemorosa* (Linnaeus).
Cultivar designation: 'Bumblesky'.

BACKGROUND OF THE INVENTION

The present invention relates to a new and distinct cultivar of ornamental Sage plant hereinafter referred to by the cultivar name *Salvia* 'Bumblesky' or as the new plant. The new plant was hybridized on May 17, 2012 at a wholesale perennial nursery in Zeeland, Mich., USA. The new plant was the result of a cross between *Salvia* 'Crystal Blue' U.S. Plant Pat. No. 26,344 and 'Sensation Deep Rose Improved' (not patented). The seeds from the cross were harvested on Aug. 7, 2012 and the single specific seedling that developed into the new *Salvia* was assigned the breeder code 12-59-3 through the evaluation process. The new plant was first selected for further evaluation in the summer of 2013 and selected for final evaluation in the summer of 2015. The first asexual propagation was performed in the summer of 2014 by shoot tip cuttings at the same nursery in Zeeland, Mich. 'Bumblesky' has proven that it is stable and reliably produces true to type plants in successive generations of asexual propagation.

No plants of *Salvia* 'Bumblesky' have been sold or disclosed in this country, or anywhere in the world, by this or any name, more than one year prior to the filing of this application, with the exception of that which was sold or disclosed either directly or indirectly from the inventor.

SUMMARY OF THE INVENTION

Plants of *Salvia* 'Bumblesky' have not been observed under all possible environmental conditions. The phenotype may vary somewhat with variations in environment such as temperature, nutrition and light intensity without, however, any variance in genotype.

*Salvia* 'Bumblesky' can be most closely compared to *Salvia* 'Crystal Blue' U.S. Plant Pat. No. 26,344, 'Sal Card 07' U.S. Plant Pat. No. 20,184, *Salvia* 'May Night' (not patented), *Salvia* 'Blue Hill' (not patented) and *Salvia* 'Sensation Sky Blue' (U.S. Plant Patent status unknown). In comparison with 'Sal Card 07' the new plant is more compact and rounded in habit and the new plant has lighter colored flowers. In comparison with 'May Night' the new plant habit is shorter and more compact, but is more branched and has larger and lighter blue-colored flowers. In comparison with 'Blue Hill', the new plant habit shorter and more compact, and the flower is a lighter blue color. Compared with 'Sensation Sky Blue' the new plant habit is slightly larger and the flower color is a lighter blue. Compared with the female parent 'Crystal Blue' the new plant is more compact habit and has lighter blue flowers. Compared with the male parent, the new plant has a larger habit than 'Sensation Deep Rose Improved', and the male parent has rose-pink flowers, whereas the new plant has light blue flowers.

The following characteristics in combination distinguish *Saliva* 'Bumblesky' as a new and distinct cultivar:

1. Small, light blue-colored flowers densely arranged in verticils;
2. Compact rounded habit and stiff, upright, heavily-branched stems;
3. Strong, vigorous and winter-hardy;
4. Rugose gray-green foliage.

BRIEF DESCRIPTION OF THE DRAWINGS

The photographs of the new plant demonstrate the unique traits and the overall appearance of *Salvia* 'Bumblesky'. The colors are as accurate as reasonably possible with color reproductions. Variation in ambient light spectrum, source and direction may cause the appearance of minor variation in color. The plant used in the photographs was a two-year old plant grown in an open, full-sun trial garden at a wholesale perennial nursery in Zeeland, Mich. with supplemental water and fertilizer when needed. No stem pinching or plant growth regulators have been used.

DETAILED BOTANICAL DESCRIPTION

Figure 1:
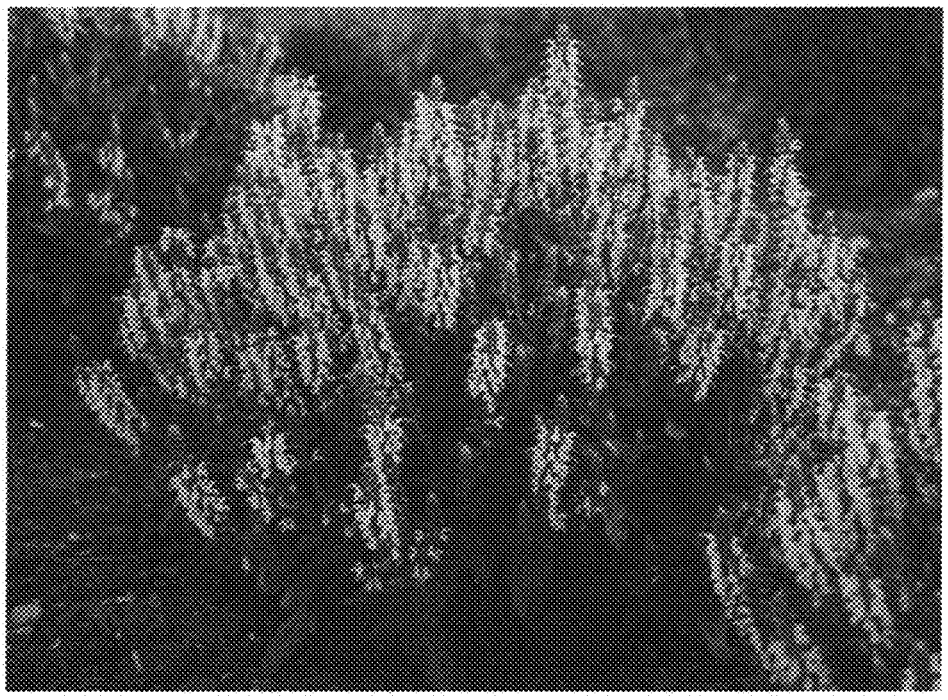
FIG. 1 shows the plant habit in full flower in a landscape.
Figure 2:
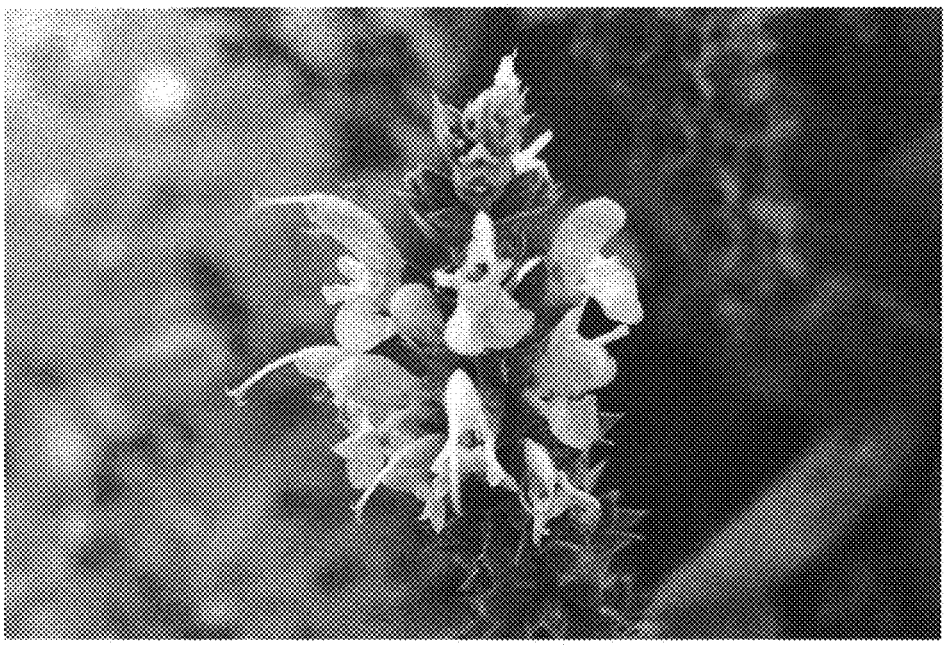
FIG. 2 shows a close-up of the flower scape with the buds and unique light blue petal color.

The following descriptions and color references except where common dictionary terms are used are based on the 2015 edition of The Royal Horticultural Society Colour Chart. *Salvia* 'Bumblesky' has not been observed under all possible environments. The phenotype may vary slightly with different growing environments such as temperature, light, fertility, soil pH, moisture and plant maturity levels, but without any change in the genotype. The following observations and size descriptions are based on two-year old plants growing both in a greenhouse with minimal shading and in an outdoor full-sun trial garden at a wholesale perennial nursery in Zeeland, Mich. Plants were given supplemental water and fertilizer but no plant growth regulators were used.

Botanical classification: *Salvia nemorosa* (Linnaeus);

Parentage: Female or seed parent is *Salvia* 'Crystal Blue'; the male or pollen parent was 'Sensation Deep Rose Improved' (not patented);

Plant habit: Winter-hardy herbaceous perennial; multi-stemmed, with basal and cauline foliage, and flowers in several tightly arranged verticils on heavily-branched upright racemes displayed above foliage; in flower with panicles about 34 cm tall and about 40 cm wide at the fullest point about 15 cm above soil; foliage extends about two-thirds of the way up the stems;

Propagation: By herbaceous tip cuttings; time to produce a rooted stems about two weeks;

Growth rate: Rapid, vigorous, finishing in from a 25 mm plug to flower in one-gallon pot in about 10 to 12 weeks, and flowering in a one-gallon pot from a dormant bare-root one-year-old plant in about 6 to 8 weeks;

Root description: Fine, well-branched; color dependent on age and soil type, from cream to dark tan in color;

Foliage: Opposite, simple, rugose, lanceolate; margin crenate, glabrous upper and lower surfaces except veins; acute apex and base cordate to auriculate with lobes sometimes overlapping; lightly puberulent abaxial and matte adaxial; leaf blades about 6.6 cm long and 3.3 cm across, decreasing in size distally; average about 5.5 cm long and 2.8 cm across; faint sage fragrance;

Foliage color: Adaxial surface nearest RHS 137A; abaxial surface nearest RHS 146B;

Venation: Reticulate; impressed on adaxial side and ridged on abaxial side; puberulent abaxial and glabrous adaxial midrib and secondary veins;

Vein color: Adaxial midrib nearest RHS 145D, main and secondary veins same color as surrounding tissue; abaxial midrib and main veins nearest RHS 145D, secondary veins nearest RHS 145C and becoming nearest RHS 146B toward leaf margin;

Petiole: Concavo-convex, pubescent along margin and puberulent abaxial and adaxial surfaces; to about 2.5 cm long and 2.0 mm wide, average 2.0 cm long and 2.0 mm wide at base;

Petiole color: Adaxial surfaces center nearest RHS 147D and margins nearest RHS 138A; abaxial center nearest RHS 145C and margins nearest RHS 138A;

Stems: Quadrangular; pubescent, to 16.0 cm long before flowers and 3.5 mm across at base;

Nodes: Five before flowering verticils; average internode length 3.2 cm; color same as stem;

Flower description: Perfect, bilabiate, verticillate with flowering generally beginning at lower verticils and advancing up the scape; with lower lip projected downward almost vertically and parallel to stem and hood petal upwardly at about 45 degree angle above horizontal; self-cleaning, petals not persistent; flowering beginning late spring for about four weeks and repeating if initial scapes removed;

Flower longevity: About four days on the plant or as cut flower;

Fragrance: No detected;

Flower buds one to two days prior to anthesis: Shape is rounded on top and slightly concave below, with rounded apex; pubescent; about 8.0 mm long, 2.5 mm tall and 1.5 mm wide;

Flower bud color: Petals variable between RHS 91B and RHS 91C; calyx distal region nearest RHS 138A, base nearest RHS 144D, with veins and distal region in more light tinted with nearest RHS N187B;

Flowers: Bilabiate corolla; zygomorphic; about 1.4 cm long from base of calyx to tip of exserted style, 8.0 mm tall and 4.0 mm wide; clustered at verticils with about six flowers per verticil;

Petals: Two; upper hood petal and lower labium petal;

Hood (upper) petal: Slightly arcuate in distal half; flattened side to side vertically, with emarginate apex and base fused with labium in basal 5.0 mm, tube diameter about 2.0 mm; puberulent outside, glabrous inside; 11.0 mm long, 3.0 mm tall and 1.0 mm across;

Labium (lower) petal: Consisting of three lobes, two upwardly projecting proximal lobes about 1.0 mm long and 1.0 mm wide at base with rounded apex, one distal lobes about 3.0 mm long 4.0 mm wide with rounded apex; distal portion of lower labium slightly concaved upwards; glabrous adaxial and microscopically puberulent abaxial; about 7.0 mm long, 4.0 mm wide at the widest portion and 4.0 mm tall;

Petal color: Both upper hood and lower labium nearest RHS 91C abaxial and nearest RHS 91D adaxial;

Androecium: Two, fused with labium, contained within hood petal;

*Filament*.—Glabrous, about 2.0 mm long and less than 0.5 mm diameter; fused about 4.0 mm from base of labium petal; curved around inside of hood petal; color proximal region nearest RHS N88D, lightening lighter than RHS 85D before stamen.

*Anther*.—Glabrous, oblong, less than 1.0 mm long and less than 0.5 mm diameter; longitudinal, dorsifixed; color mixture between RHS 160D and RHS 157A.

*Pollen*.—Globose, less than 0.5 mm circumference; color nearest RHS 11B.

Gynoecium: One, curved around inside of hood petal; total about 1.5 cm long;

*Style*.—About 13.0 mm long and less than 0.5 mm diameter; color nearest RHS NN155D at base, darkening distally to nearest RHS 85C before stigma split.

*Stigma*.—Split in two and curved in the terminal 1.0 mm; apex pointed; color between RHS 84A and RHS N82B.

*Ovary*.—Superior; color nearest RHS 145A.

*Fruit*.—Not yet observed.

Calyx: Five sepals, three upper and two lower, campanulate, apex acute; fused base; persistent; tube about 5.0 mm long and 2.0 mm wide; lower cleft about 2.0 mm deep between lobes and upper and lower set; upper set of three fused to closer than 0.5 mm of apex;

Calyx color: Abaxial nearest RHS 138B with darker veins of RHS 137A; adaxial nearest RHS 148D with darker veins of RHS 137A;

Bracts: Each verticil subtended by two opposite bracts; apex acuminate, base truncate, shape nearly cordate; margin entire, ciliolate, and glabrous above and below; bract size up to 8.0 mm long and 9.0 mm wide, decreasing distally; color of both surfaces nearest RHS 137A with center and base veins nearest RHS 145D;

Peduncles: Quadrangular in cross section, about 16 per plant; strong; mostly upright, up to 60 cm tall and 5.0 mm across; finely pubescent; heavily branched with branches at about 45 degrees above horizontal at three nodes below flowers; branches to about 7.5 cm long and 2.0 mm across; average space between verticils 0.6 cm;

Peduncle color: Nearest RHS 138A in upper and lower regions;

Pedicels: Cylindrical, about 1.0 mm long and 0.5 mm diameter; puberulent; horizontal to about 20 degrees above horizontal;

Pedicel color: Nearest RHS 146D;

Disease and pest resistance: Plants of *Salvia* 'Bumblesky' perform best with adequate moisture and good drainage, but tolerate low moisture once established; hardy from USDA zone 3 to 8; resistance to diseases and pests beyond that common to *Salvia* has not been noted.

It is claimed:

1. The new and distinct perennial *Salvia* plant named 'Bumblesky' as herein described and illustrated useful for landscaping as a specimen plant, en masse or as a cut flower.

* * * * *